United States Patent [19]

Rawlings et al.

[11] Patent Number: 4,711,849
[45] Date of Patent: Dec. 8, 1987

[54] CONSTRUCTION OF SELECTABLE SHUTTLE CLONING VECTORS FOR THIOBACILLUS FERROOXIDANS

[75] Inventors: Douglas E. Rawlings; David R. Woods, both of Rondebosch, South Africa

[73] Assignee: General Mining Union Corporation, Limited, Johannesburg, South Africa

[21] Appl. No.: 667,254

[22] Filed: Nov. 1, 1984

[51] Int. Cl.⁴ .................. C12P 19/34; C12N 15/00; C12N 7/00
[52] U.S. Cl. .................. 435/91; 435/172.3; 435/317.1; 935/22; 935/29
[58] Field of Search .................. 435/172.3, 91, 317; 935/29

[56] References Cited

U.S. PATENT DOCUMENTS 4,340,674  7/1982  Maris et al. .................. 435/172

FOREIGN PATENT DOCUMENTS 2512058  4/1983  France .

OTHER PUBLICATIONS

Kreft, J. et al., Mol. Gen. Genet., 1983, pp. 384–389.
Rawlings, D. E. et al., Abstract in French in International Symposium on Biohydrometallurgy, May 1, 1983, pp. 555–570.
Holmes et al., J. Bacteriol. 157(1): 324–326, 1984 (Jan.).
Bolivar, Life Sciences 25:807–818, 1979.
Martin et al., Con. J. Microbiol, 27: 850–853, 1981.
Rawlings, D. E. et al., "Expression of *Thiobacillus ferrooxidans* Origin of Replication in *Escherichia coli*", Journal of Bacteriology, vol. 158, No. 2, May, 1984, pp. 737–738.
Rawlings, D. E., et al., "Construction of arsenic-resistant *Thiobacillus ferrooxidans* recombinant plasmids and the expression of autotrophic plasmid genes in a heterotrophic cell-free system", Journal of Biotechnology, 1 (1984) 129–133.
Rawlings, D. C., et al., "Mobilization of *Thiobacillus ferrooxidans* plasmids among *Escherichia coli* Strains, Applied and Environmental Microbiology, vol. 49, No. 5, 1985, pp. 1323–1325.
Barros, M. E. C., et al., "Production and Regeneration of *Thiobacillus ferrooxidans* Spheroplasts, Applied and Environmental Microbiology, vol. 50, No. 3, Sep. 1985, pp. 721–723.

*Primary Examiner*—Thomas G. Wiseman
*Assistant Examiner*—Thomas Mays

[57] ABSTRACT

The plasmids pDR401 and pDR412 are disclosed which contain a selectable chloramphenicol resistance gene and which are able to replicate in both *T. ferrooxidans* and *E. coli*. A process for constructing the plasmids is also described.

6 Claims, 1 Drawing Figure

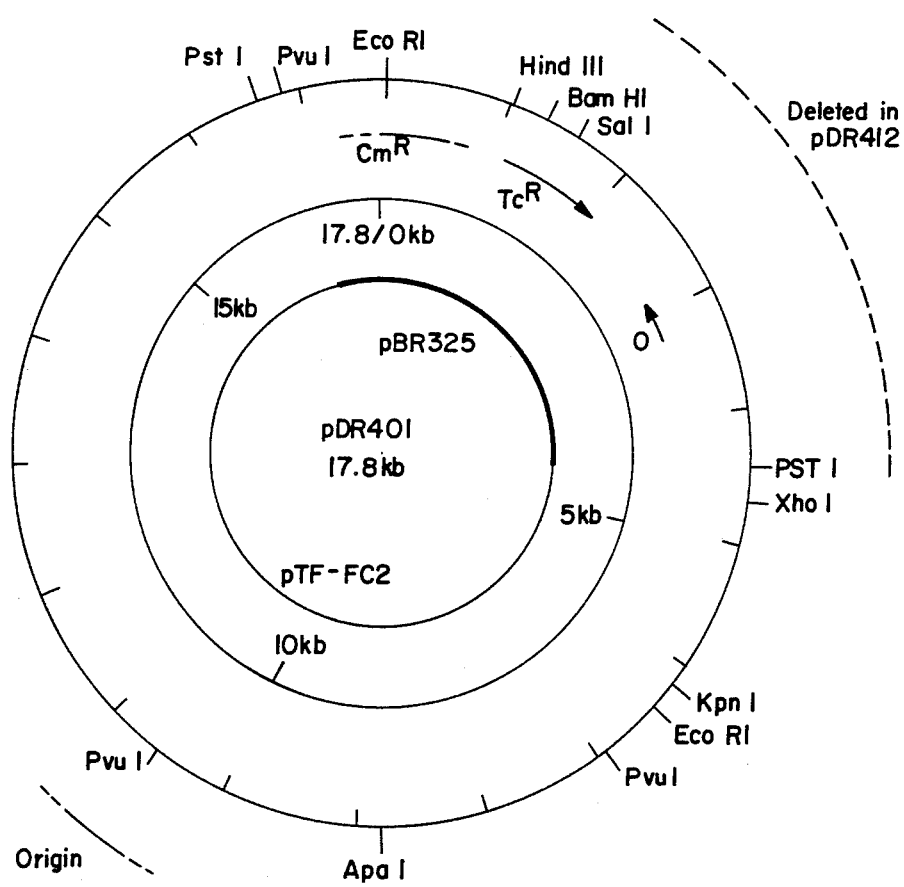

CONSTRUCTION OF SELECTABLE SHUTTLE CLONING VECTORS FOR THIOBACILLUS FERROOXIDANS

BACKGROUND OF THE INVENTION

This invention relates to the construction of recombinant DNA cloning plasmid vectors for *Thiobacillus ferrooxidans* which contain a selectable chloramphenicol resistance gene and are able to replicate in both *T. ferrooxidans* and *Escherichia coli*.

Although selectable cloning vectors have been constructed for other bacteria, there are, to the applicant's knowledge, no previous reports of the construction of selectable cloning vectors for *T. ferrooxidans* which can also replicate in *E. coli*.

SUMMARY OF THE INVENTION

According to the present invention a plasmid vector is constructed by extracting a cryptic DNA plasmid from a *T. ferrooxidans* strain, cleaving the *T. ferrooxidans* plasmid and a second plasmid which contains a chloramphenicol resistance gene with the same restriction enzyme, and ligating the plasmids to form a recombinant plasmid.

The second plasmid may be the plasmid pBR325, although other suitable plasmids could possibly by used in place of pBR 325.

The resulting recombinant plasmid, pDR401, replicated in *E. coli*.

According to a further aspect of the invention the pDR401 plasmid may be reisolated and modified by cleavage with at least one restriction enzyme to remove the *E. coli* origin of replication.

The deleted recombinant plasmid, pDR412, contains the chloramphenicol resistance gene and replicated in *E. coli* using the *T. ferrooxidans* origin of replication.

The invention also extends to the recombinant plasmids, pDR401 and pDR412, as herein defined, which are novel selectable shuttle vectors and which can be used for genetic manipulation experiments involving *T. ferrooxidans* and *E. coli*.

Thus the invention provides a plasmid pDR401 which has a size of about 17.8 kb and which is divided into three fragments having the sizes 3.5 kb, 6.2 kb and 8.1 kb, respectively, by the restriction enzyme Pvu1.

The invention also provides a plasmid pDR412 which has a size of about 14.8 kb and which is divided into three fragments having the sizes 3.5 kb, 5.1 kb and 6.2 kb, respectively, by the restriction enzyme Pvu1.

DESCRIPTION OF PREFERRED EMBODIMENT

An example of the invention is described with reference to the accompanying drawing which illustrates restriction maps of the cryptic plasmid, and the recombinant plasmids of the invention.

A 12.4 kilobase (kb) cryptic plasmid, pTF-FC2, was extracted from a *T. ferrooxidans* FC strain isolated from acid leach liquor from Fairview Mine, General Mining Union Corporation Limited, South Africa. Restriction mapping of pTF-FC2 shows that it has unique Pst1, Xho1, Kpn1, EcoR1, Apa1, restriction sites and two Pvu1 restriction sites, (refer to the accompanying drawing).

A recombinant plasmid, pDR401, was constructed by insertion of the *E. coli* plasmid, pBR325, into the Pst1 site of pTF-FC2. pBR325 contains the genes for ampicillin (Ap), chloramphenicol (Cm) and tetracycline (Tc) resistance. Cloning at the Pst1 site insertionally inactivated the $Ap^R$ gene and *E. coli* transformants which were $Cm^R$, $Tc^R$ and $Ap^S$ were isolated. The recombinant plasmid pDR401 (about 17.8 kb) was extracted from the *E. coli* transformants and characterized by restriction analysis. This novel recombinant plasmid contains the genes for $Cm^R$ and $Tc^R$ and is able to replicate in *T. ferrooxidans* and *E. coli*.

A deletion plasmid, pDR412 (about 14.8 kb), was constructed following Sal1/Xho1 digestion of pDR401 and removal of the Sal1/Xho1 fragment (about 3.0 kb) which contained the pBR325 origin of replication and approximately half of the Tc gene, and a 0.3 kb piece of the *T. ferrooxidans* pTF-FC2 DNA. Restriction analysis confirmed that the Sal1/Xho1 3,1 kb fragment had been deleted in the plasmid pDR412. This novel recombinant plasmid contains the gene for $Cm^R$ and is able to replicate in *T. ferrooxidans* and *E. coli*.

The two plasmids pDR401 and pDR412 were characterized by endonucleolytic cleavage with a restriction enzyme.

Thus the restriction enzyme Pvu1 cleaves the plasmid pDR401 into three fragments having the sizes 3.5 kb, 6.2 kb and 8.1 kb, respectively.

The same restriction enzyme Pvu1 cleaves the plasmid pDR412 into three fragments having the sizes 3.5 kb, 5.1 kb and 6.2 kb, respectively.

The *T. Ferrooxidans* strain has been deposited with the American Type Culture Collection, 12301 Parklawn Drive, Rockville, MD 20852 and has been assigned ATCC number 39838. It has a taxonometric description as follows: It is an autotrophic aerobic, Gram-negative, rod shaped bacterium. It is able to oxidize ferrous iron to ferric iron and reduced and partially reduced sulfur compounds to sulfuric acid. Its optimum pH is between 1.6 and 2.2 and its optimum temperature is between 25° C. and 30° C. It has a G-C ratio of 59–60 mol percent.

What is claimed is:

1. A method of constructing resistance vectors for Thiobacillus ferrooxidans which includes the steps of;
   (a) extracting a cryptic DNA plasmid from a *T. ferrooxidans* strain, cleaving the *T. ferrooxidans* plasmid and a second plasmid which contains a chloramphenicol resistance gene and an *E. coli* origin of replication with the same restriction enzyme, and ligating the plasmids to form a recombinant plasmid,
   (b) transforming *E. coli* cells with the recombinant plasmid and selecting for chloramphenicol resistant transformants capable of replication in *E. coli* and,
   (c) removing the *E. coli* origin of replication from the recombinant plasmid by cleavage with a restriction enzyme to form a deleted recombinant plasmid, capable of replication both in *E. coli* and *T. ferrooxidans*.

2. A method according to claim 1 wherein the cryptic DNA plasmid is pTF-FC2 having the size 12.4 kb.

3. A method according to claim 2 wherein the second plasmid is pBR325.

4. A method according to claim 3 wherein the pBR325 plasmid is inserted into the Pst1 site of the pTF-FC2 plasmid.

5. A method according to claim 1 wherein the second cleaving step includes the removal of a fragment of about 3.0 kb, which contains the origin of replication of the second plasmid, from the recombinant plasmid.

6. A plasmid pDR412 which has a size of about 14.8 kb and which is divided into three fragments having the sizes 3.5 kb, 5.1 kb and 6.2 kb, respectively, by the restriction enzyme Pvu1.

* * * * *

UNITED STATES PATENT AND TRADEMARK OFFICE
CERTIFICATE OF CORRECTION

PATENT NO. : 4,711,849
DATED : December 8, 1987
INVENTOR(S) : DOUGLAS E. RAWLINGS ET AL It is certified that error appears in the above-identified patent and that said Letters Patent is hereby corrected as shown below:

Change Claim 1 to be as follows:

1. A method of constructing resistance vectors for Thiobacillus ferrooxidans which includes the steps of:

a) creating a recombinant plasmid by selecting a cryptic DNA plasmid from a T. ferrooxidans strain and cleaving said cryptic DNA plasmid with a restriction enzyme and ligating to a second DNA plasmid which contains both a chloramphenicol resistance gene and an E. coli origin of replication and which has been cleaved with the same restriction enzyme, b) isolating said recombinant plasmid by transforming E. coli cells with said recombinant plasmid and selecting for chloramphenicol resistant transformants capable of replication in E. coli,

UNITED STATES PATENT AND TRADEMARK OFFICE
CERTIFICATE OF CORRECTION

PATENT NO. : 4,711,849
DATED : December 8, 1987
INVENTOR(S) : DOUGLAS E. RAWLINGS ET AL Page 2 of 2

It is certified that error appears in the above-identified patent and that said Letters Patent is hereby corrected as shown below:

c) removing the *E. coli* origin of replication from said recombinant plasmid of selected transformants by cleavage with a restriction enzyme to form a deleted recombinant plasmid, capable of replication both in *E. coli* and *T. ferrooxidans* and, d) isolating said deleted recombinant plasmid.

Claim 3, line 1 (column 2, line 55), after "second" insert --DNA--

Signed and Sealed this

Twenty-sixth Day of April, 1988

Attest:

DONALD J. QUIGG

Attesting Officer      Commissioner of Patents and Trademarks